US008038659B2

(12) United States Patent
Boyden et al.

(10) Patent No.: US 8,038,659 B2
(45) Date of Patent: Oct. 18, 2011

(54) DISINTEGRATING DIGESTIVE TRACT INTERACTION SYSTEM

(75) Inventors: Edward S. Boyden, Cambridge, MA (US); Roderick A. Hyde, Redmond, WA (US); Muriel Y. Ishikawa, Livermore, CA (US); Jordin T. Kare, Seattle, WA (US); Robert Langer, Newton, MA (US); Eric C. Leuthardt, St. Louis, MO (US); Dennis J. Rivet, Portsmouth, VA (US); Michael A. Smith, Phoenix, AZ (US); Charles Whitmer, North Bend, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 851 days.

(21) Appl. No.: 11/975,371

(22) Filed: Oct. 17, 2007

(65) Prior Publication Data

US 2009/0105531 A1    Apr. 23, 2009

(51) Int. Cl.
*A61M 31/00* (2006.01)
(52) U.S. Cl. ....................................... 604/285; 604/516
(58) Field of Classification Search .................. 600/101, 600/128, 130, 139–142; 604/93.01, 285, 604/503, 516, 890.1, 891.1
See application file for complete search history.

(56) References Cited

U.S. PATENT DOCUMENTS

| | | | |
|---|---|---|---|
| 4,595,583 A | 6/1986 | Eckenhoff et al. | |
| 4,925,446 A | 5/1990 | Garay et al. | |
| 5,354,264 A | 10/1994 | Bae et al. | |
| 5,879,325 A | 3/1999 | Lindström et al. | |
| 5,938,654 A | 8/1999 | Wong et al. | |
| 6,283,953 B1 | 9/2001 | Ayer et al. | |
| 6,689,056 B1 | 2/2004 | Kilcoyne et al. | |
| 7,857,767 B2 | 12/2010 | Ferren et al. | |
| 2003/0023150 A1* | 1/2003 | Yokoi et al. | 600/300 |
| 2005/0246037 A1 | 11/2005 | Starkebaum | |
| 2007/0088334 A1 | 4/2007 | Hillis et al. | |
| 2007/0106226 A1 | 5/2007 | Croll et al. | |
| 2008/0214619 A1 | 9/2008 | Wolfe et al. | |

OTHER PUBLICATIONS

Duchene, D. et al.; "Pharmaceutical and Medical Aspects of Bioadhesive Systems for Drug Administration"; Drug Development and Industrial Pharmacy; 1988; pp. 283-318; vol. 14, No. 2&3; Marcel Dekker, Inc.

Quirini, Marco et al.; "Design of a Pill-Sized 12-Legged Endoscopic Capsule Robot"; IEEE International Conference on Robotics and Automation; Apr. 10-14, 2007; pp. 1856-1862; Roma, Italy.

Rentschler, Mark E. et al.; "Natural Orifice Surgery With an Endoluminal Mobile Robot"; SAGES Meeting; 2006; pp. 1-14; located at: http://robots.unl.edu/Files/Papers2/Rentschler_Natural_Orifice_Robot_with_figures.pdf.

(Continued)

*Primary Examiner* — Nicholas D Lucchesi
*Assistant Examiner* — Nathan R Price (57) ABSTRACT

Systems and methods are described for configuring several modules each individually small enough to pass through a digestive tract; and a tether or other means for releasably configuring at least the several modules in a group. Such a tether may (directly or indirectly) couple some of the modules via at least a gap in another module from which the tether may slip free, in some embodiments. Such methods may include modes of administering a medication or otherwise taking an action in response to the one or more phenomena.

24 Claims, 7 Drawing Sheets

OTHER PUBLICATIONS

Excerpt from The American Heritage Dictionary of the English Language; bearing a date of 2009; Printed on Jan. 19, 2011; located at: http://education.yahoo.com/reference/dictionary/entry/moor; total of 2 pages (as provided by examiner).

* cited by examiner

DISINTEGRATING DIGESTIVE TRACT INTERACTION SYSTEM

CROSS-REFERENCE TO RELATED APPLICATIONS

The present application is related to the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS:

1. For purposes of the USPTO extra-statutory requirements, the present application relates to U.S. patent application Ser. No. 11/414,164, entitled IMAGING VIA BLOOD VESSELS, naming Edward K.Y. Jung, Eric C. Leuthardt, Royce A. Levien, Robert W. Lord, Mark A. Malamud, John D. Rinaldo, Jr., Clarence T. Tegreene and Lowell L. Wood, Jr. as inventors, filed 28, Apr., 2006.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

In one aspect, a digestive tract interaction system includes but is not limited to several modules each individually small enough to pass through a digestive tract; and a tether or other means for releasably configuring at least the several modules in a group. Such a tether may (directly or indirectly) couple some of the modules via at least a gap in another module from which the tether may slip free, in some embodiments.

In another aspect, a digestive tract interaction method includes but is not limited to reacting to or otherwise detecting one or more phenomena in a digestive tract and administering a medication or otherwise taking an action in response to the one or more phenomena. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In yet another aspect, a digestive tract interaction system includes but is not limited to circuitry for detecting one or more phenomena in a digestive tract and circuitry for energizing an actuator or otherwise taking an action in response to the one or more phenomena. In addition to the foregoing, other system aspects are described in the claims, drawings, and text forming a part of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

DETAILED DESCRIPTION

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In the following detailed description, reference is made to the accompanying drawings, which form a part hereof. The use of the same symbols in different drawings typically indicates similar or identical items. The illustrative embodiments described in the detailed description, drawings, and claims are not meant to be limiting. Other embodiments may be utilized, and other changes may be made, without departing from the spirit or scope of the subject matter presented here.

Following are a series of systems and flowcharts depicting implementations of processes. For ease of understanding, the flowcharts are organized such that the initial flowcharts present implementations via an initial "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 1:
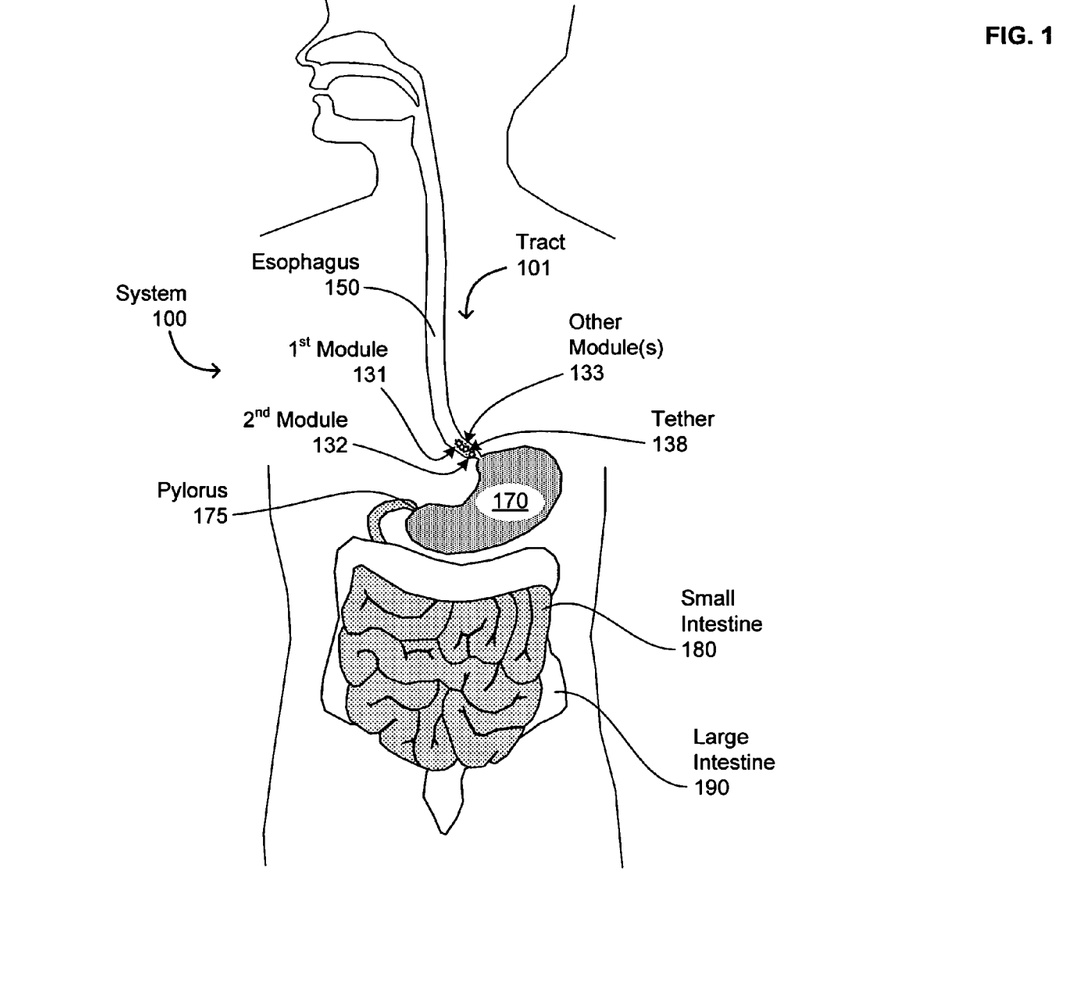
FIG. 1 shows a digestive tract interaction system including several modules each individually small enough to pass through a digestive tract.

With reference now to FIG. 1, shown is an example of a system that may serve as a context for introducing one or more processes and/or devices described herein. As shown system 100 may (optionally) include a "1$^{st}$" module 131, a "2$^{nd}$" module 132, and one or more "other" modules 133 that are of roughly comparable size (e.g. within 1-2 orders of magnitude) and each individually small enough to pass through a digestive tract 101 comprising esophagus 150, gastric compartment 170, pylorus 175, small intestine 180, and large intestine 190. Such "1$^{st}$" and "2$^{nd}$" modules 131, 132 are coupled indirectly via at least one tether 138 passing through the "other" module(s) 133, tether 138 configured to slip free from the "other" module(s) 133 if and when the "1$^{st}$" and "2$^{nd}$" modules 131, 132 decouple. This may occur, for example, in circumstances in which such tether(s) 138 dissolve, break, or are otherwise released from one or both end-most modules.

Figure 2:
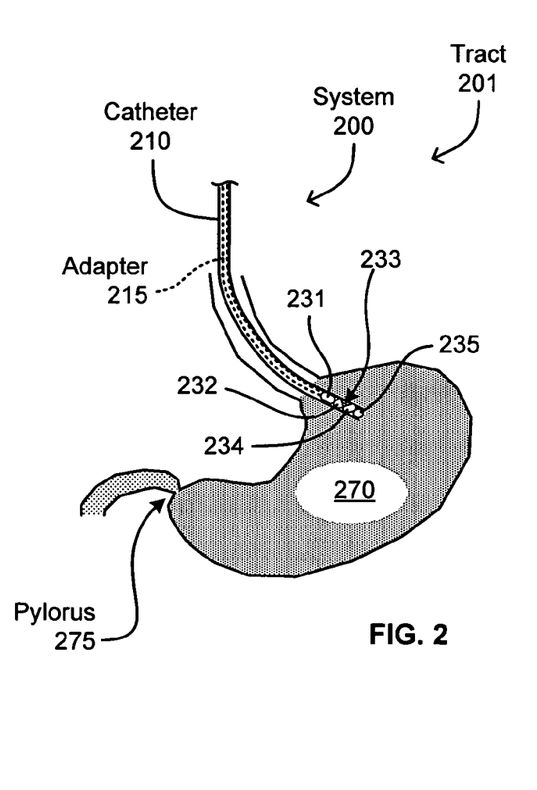
FIG. 2 shows another interaction system including several modules being deployed into a digestive tract through a catheter.

With reference now to FIG. 2, shown is an example of a system that may serve as a context for introducing one or more processes and/or devices described herein. As shown system 200 may (optionally) include a catheter 210 containing several modules 231, 232, 234, 235 each within gastric compartment 270 and small enough to pass through tract 201 individually. In some variants, catheter 210 may be small enough to pass through a nasal passage, for example. Alternatively or additionally, catheter 210 may comprise one or more inner sleeves or other adapters 215 configured for use in manipulating one or more modules in situ, such as by urging module 231 outward, by applying an adhesive, by cutting a tether, or for other operations as described herein in various implementations. As shown, most or all of such modules 231, 232, 234, 235 are strung onto a common tether 233, preferably in a configuration that is dosed, sequenced, or otherwise tailored for administration to a specific patient, and optionally within a soluble capsule. In some variants, the tether is strung through a non-axial portion of one or more intermediate modules 232, 234 so that tension in the tether tends to urge the grouping of modules to become less coaxial. Such tension can be preloaded in an elastic length of tether 233, for example, so that a shape change occurs immediately in response to an expulsion from catheter 210 or a capsule, or later in response to detectable environmental changes. Such shape changes may be configured to occur in response a sufficiently-long exposure to an acidic and/or aqueous environment, a body-temperature environment, an electrically conductive environment, or other such environmental circumstances indicative of entry into a specific portion of a digestive tract of a given subject. Such shape changes in gastric compartment 270 may cause a grouping of several modules 231, 232, 234, 235 to become too large to pass through pylorus 275 and too irregular for them to become a problematic blockage. For example, some or all of the modules 231, 232, 234, 235 may be configured to swell or otherwise remove slack from and/or introduce tension into tether 233. If tether 233 is configured in a loop, for example, such swelling will tend to cause the modules to become less collinear, and thus less likely for pylorus 275 to be blocked.

In most contexts, a single module is "small enough to pass through a digestive tract" if a physician, veterinarian, or other skilled care provider would consider it safe for an inert item of that size to pass through the tract without becoming an obstruction. For most human beings and other mammals this corresponds with a module that is narrower than an eyeball (e.g., at most about 2 centimeters wide) and at most a few times as long as the eyeball (e.g., up to several centimeters long), and a slightly larger size for highly pliable modules. An unobstructed, normal digestive tract in a human adult of typical size, for example, may reasonably be expected to pass an inert module as large as a penny or AAA battery but not one as large as a typical pen or golf ball.

In most contexts, a module may be described as "at least 10% as large" as an item if the module is at least 10% as long as the item. The module is likewise "at least 10% as large" as the item if the module is at least 10% as voluminous as the item, taking the volume of each to include the volume of any bores or other regions of concavity therein. In an embodiment in which module 232 is "at least 10% as large" as module 231, for example, either of these module may accordingly be larger than the other in terms of length or volume.

In most contexts, a tether is "operable for coupling" modules via a gap if the tether helps to maintain the modules in a vicinity of each other by extending at least partly into the gap. One or more such tethers may wrap around several such modules, for example, securing them at least partly within one or more recesses of a ring, spool, or cup.

In most contexts, a tether segment is "small enough to slip free" from a module if the module is free to slide along and/or away from the tether segment by virtue of one or more bores or other recessed portions of the module being large enough not to grip the tether segment. In a context in which a tether segment breaks away or is otherwise released from a "first" module, for example, a "third" module may (optionally) be configured to drift free from the "first" and "second" modules as well in response to mechanical action in the digestive tract.

Those skilled in the art will recognize sufficient and useful clarity in these terms to make and use many structures they describe without undue experimentation, in light of these teachings. Those skilled in the art will likewise recognize a variety of safe materials suitable for implementing structures as described herein without undue experimentation, in light of these teachings.

In some variants, system 200 is initially configured so that catheter 210 contains several modules 231, 232, 234, 235 each small enough to pass (safely) through digestive tract 201. As shown, "second" module 235 may be sized within an order of magnitude of "first" module 231, at least in terms of length, and/or with "second" module 235 somewhat shorter than "first" module 231. Alternatively or additionally, "third" module 234 may (optionally) be at least half as voluminous as "first" and/or "second" modules 231, 235. One or more instances of intermediate modules 232, 234 may (optionally) each comprise a unitary body having an overall average density smaller than 0.9 grams per milliliter, such modules tending to remain in gastric compartment 270 for a time even after tether 233 no longer operates.

Figure 3:
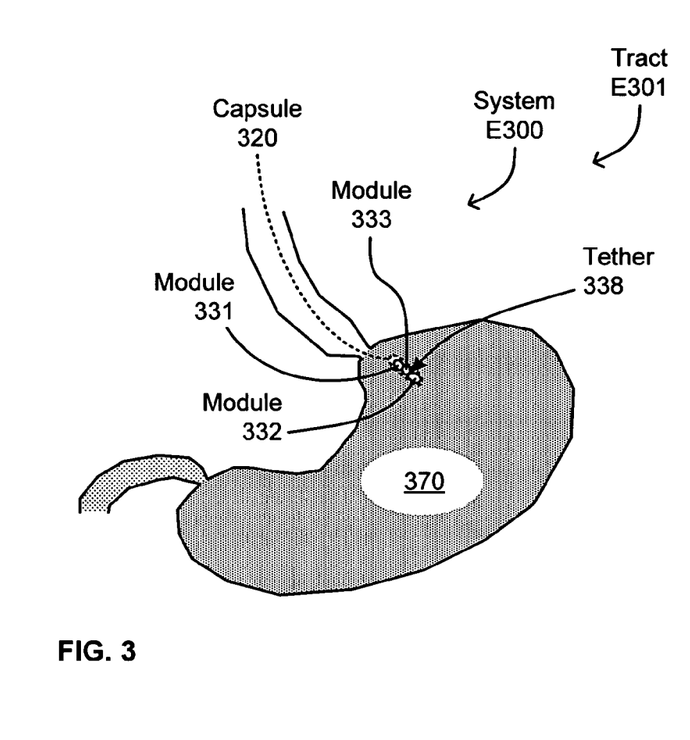
FIG. 3 shows a capsule containing several modules each small enough to pass through a digestive tract individually.

With reference now to FIG. 3, shown is an example of a system that may serve as a context for introducing one or more processes and/or devices described herein. As shown system 300 may (optionally) include a capsule 320 containing a containing several modules 331, 332, 333 each just above gastric compartment 370 and small enough to pass through tract 301 individually. In various respective embodiments as described herein, capsule 320 may optionally be small enough to pass through catheter 210 (from FIG. 2) and into compartment 370 or may optionally be small enough to be swallowed. At least modules 331, 332, 333 may (optionally) be selected according to one or more of an age or other patient attribute such as a size, shape, dosage profile, or condition of tract 301. Alternatively or additionally, tether 338 used to bind such modules, optionally passing along or through a non-axial portion of one or more intermediate modules 333 so that introducing tension into the tether tends to cause system 300 to become less coaxial, optionally in response to capsule 320 collapsing. Some or all of modules 331, 332, 333 and tether 338 may be rotationally asymmetric, tending to cause system 300 to expand in a specific relative alignment such as are described herein.

Figure 4:
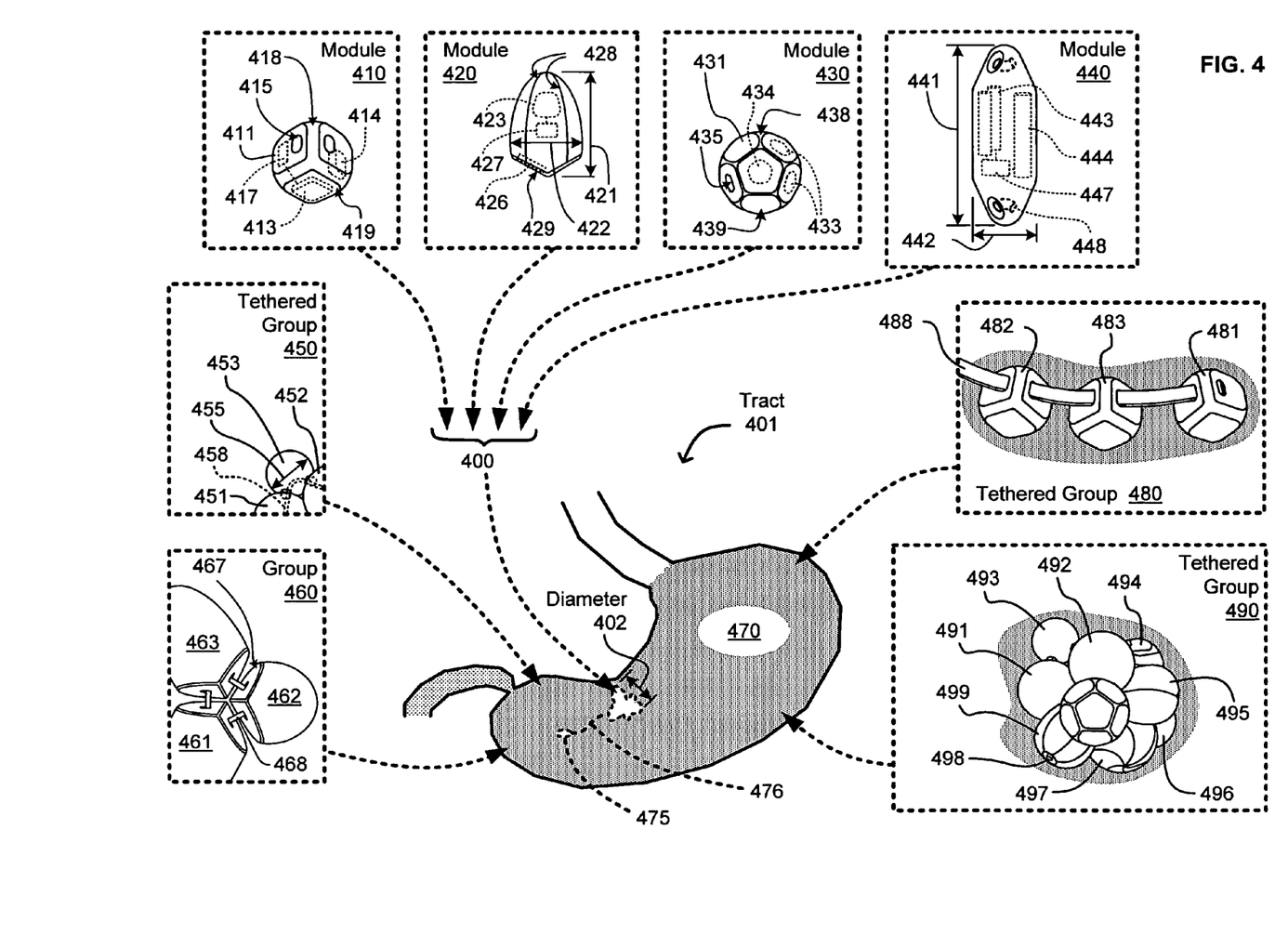
FIG. 4 shows several configurations of modules (in tethered groups, e.g.) suitable for deployment in a gastric compartment.

With reference now to FIG. 4, shown is an example of a system that may serve as a context for introducing one or more processes and/or devices described herein. As shown digestive tract 401 may include gastric compartment 470 containing one or more systems 400 such as tethered groups 450, 460, 480, 490. Each such system 400 may include one or more instances of modules 410, 420, 430, 440 as shown, for example, in a sufficient number so that system 400 has an effective cross-sectional diameter 402 too large to permit exit from gastric compartment 470 in any orientation. Some embodiments of system 400 may further comprise one or more additional modules 475 coupled with such a group by surgical thread or a similarly flexible tether 476 about 1 centimeter or more in length.

System 400 may include one or more modules 410 each comprising a cube-like unitary body 411 with six primary external surfaces 419 all bounded by a substantially convex external surface 418. Module 410 may further include one or more instances of bores 415 or other gaps configured to facilitate passage or other guidance of one or more tethers as described herein. Module 410 may also include one or more instances of (incremental) dispensers 413, 414, fluidic access to at least some of which may be controlled by circuitry 417 as described herein.

Alternatively or additionally, system 400 may (optionally) include one or more modules 420, an instance of which is shown at a somewhat magnified scale similar to that of module 410. Module 420 may comprise an oblong unitary body having a length 421 of about 1 millimeter or larger, and at least 10% greater than its cross-sectional diameter 422. The body is bounded by an upper surface having (at least somewhat) longitudinal ribs 428 as well as a plurality of other faces 429. At least one such face 429 may be situated adjacent one or more flux-guiding elements 426 operable for responding to a magnetic field within a portion of the digestive tract. Such an instance may thus tend to align (or resist misalignment) with one or more other modules of system 400, for example, if either is implemented as a permanent magnet or electromagnet. This can be particularly useful for controlling a mode of expansion in embodiments like that of facing group 460 in which opposite ends of the tether are situated in different modules, for example. While in the digestive tract, moreover, such flux-guiding elements may be safely and reliably drawn to a tract wall, for example, by providing a strong magnetic field from outside the digestive tract. Module 420 may likewise include one or more instances of dispensers 423, fluidic access to at least some of which may be controlled by circuitry 427 as described herein.

Alternatively or additionally, system 400 may (optionally) include one or more modules 430, an instance of which is shown at a somewhat magnified scale similar to those of other modules 410, 420 described above. Module 430 as shown has a unitary, substantially polyhedral body 431 with one or more convex external surfaces 438 and several other surfaces 439. (In some embodiments, such other surfaces 439 may each comprise saddle regions, recesses, or otherwise structured surfaces as described herein.) Module 430 may include one or more instances of passive dispensers 433 each containing 1-15 grams of medicinal material configured to dissolve somewhat uniformly in gastric compartment 470 over one or more days, weeks, or months. Module 430 may likewise include one or more instances of dispensers 433, 434 and/or rotationally asymmetric gaps 435 for accommodating various tether configurations as described herein.

Alternatively or additionally, system 400 may (optionally) include one or more modules 440, an instance of which is shown at a somewhat magnified scale similar to those of other modules 410, 420, 430 described above. Module 440 may (optionally) comprise a unitary body having an overall average density smaller than 0.9 grams per milliliter and/or a cross-sectional diameter 442 larger than one millimeter. Alternatively or additionally, module 440 may include one or more passages 448 or other gaps collectively sufficient for receiving more than one tether or tether winding. Module 440 may likewise include one or more instances of dispensers 443, 444, fluidic access to at least some of which may be controlled by circuitry 447 as described herein.

In some embodiments, system 400 may be configured so that the "first" module comprises module 410, so that the "second" module comprises module 420, and so that the "third" module comprises module 430, all coupled by a single common tether. In some such embodiments, the relative scaling of modules 410, 420, 430 is such that "second" module 420 (i.e. at length 421) is at least half as long and/or voluminous as "first" module 410. Alternatively or additionally, "third" module 430 may (optionally) be made larger so that it is more voluminous than "first" module 410 and/or "second" module 420. In some variants, moreover, system 400 may further comprise one or more instances of module 440 as shown, a "fourth" module having a length 441 more than twice the width thereof. Alternatively or additionally, tract 401 may (optionally) contain tethered group 450 comprising several modules 451, 452, 453 bound together by a single common tether 458. Tethered group 450 may likewise include other modules, some or all of which may optionally be bound by other tethers (not shown) to create a desired configuration. In some embodiments, module 453 may have a cross-sectional diameter 455 larger than one millimeter, optionally 2-5 millimeters or larger.

Alternatively or additionally, tract 401 may (optionally) contain group 460 comprising several modules 461, 462, 463 bound together by a single, primarily elastic tether 468. (Group 460 is shown in tension to expose a plurality of substantially flat faces 467 on each module.) In some embodiments, facing group 460 is configured so that the "first" module comprises module 461 and so that the "third" module comprises module 463, and so that one or both of these implement module 420. Module 461 may (optionally) comprise one or more instances of dispenser 423 containing a total of 1-15 grams of medicinal material, for example, such as an antibiotic or statin. Moreover in some variants "third" module 463 may be more than half as voluminous as, or may be more voluminous than, "first" module 461 and/or "second" module 462. Alternatively or additionally, "third" module 463 may be at least half as long as, or may be longer than, "first" module 461 and/or "second" module 462.

Alternatively or additionally, tract 401 may (optionally) contain tethered group 480 comprising several modules 481, 482, 483 (each small enough to pass through tract 401 individually but prevented from such passage by virtue of being) bound together by a single common tether 488. Any or all of modules 481, 482, 483 may be configured as instances of module 410, each optionally implementing circuitry 417, dispenser 413, or other attributes of module 410 as described herein. As shown, modules 481-483 may be supported along at least a rotationally asymmetric portion of tether 488. Alternatively or additionally, the "third" module 483 may be at least half as voluminous as the "second" module 482.

Alternatively or additionally, tract 401 may (optionally) contain tethered group 490 comprising several modules 491, 492, 493, 494, 495, 496, 497, 499, at least some of which are small enough to pass through tract 401 individually but prevented from such passage by virtue of being bound together in tethered group 490. Any or all of modules 491-497 and 499 may be configured as instances of other modules described herein. Tether 498 binds together at least a "first" module 499 and some of the other modules 491-497. Alternatively or additionally, as shown, "first" and/or "second" ones of modules 494-498 may each be more than twice as long as each respective width thereof.

Figure 5:
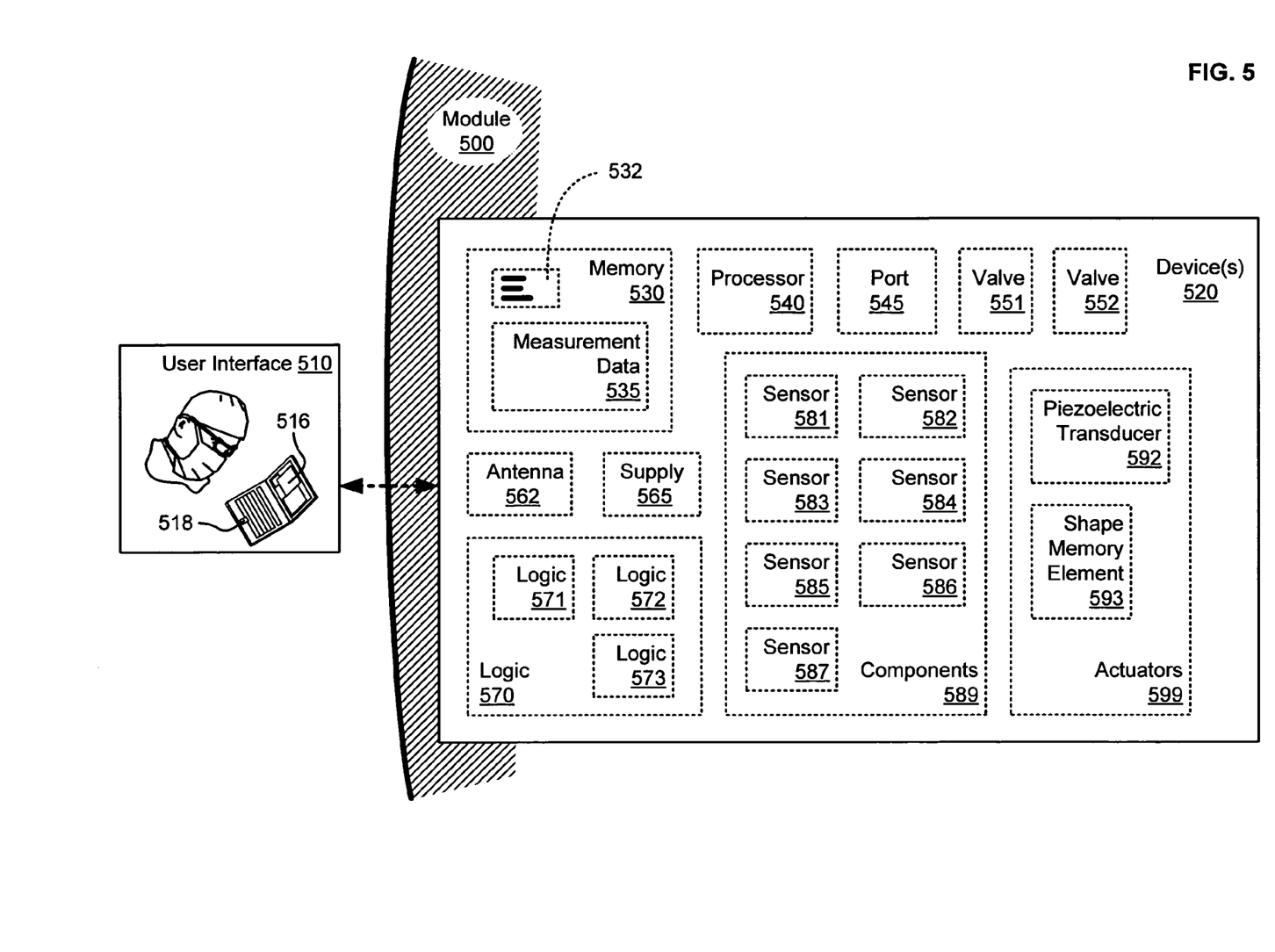
FIG. 5 shows a module that may include one or more instances of integrated circuitry or other devices that may be operable to provide output to or receive input from a user interface.

With reference now to FIG. 5, shown is an example of a system that may serve as a context for introducing one or more processes and/or devices described herein. As shown module 500 may include one or more instances of integrated circuitry or other devices 520 that may be operable to provide output 516 to and/or receive input 518 from a user interface 510 external to module 500 (via one or more antennas 562 or other ports 545). In various embodiments, for example, device(s) 520 may include one or more instances of code 532 or measurement data 535 in memory 530; processors 540; ports 545; microfluidic or other valves 551, 552; antennas 562; supplies 565; firmware, circuitry, or other logic 571, 572, 573 (such as code 532 or other software logic 570 resident in memory 530); sensors 581, 582, 583, 584, 585, 586, 587 or other such components 589 suitable for detection of physical phenomena or conditions; or piezoelectric transducers 592, shape memory elements 593, microelectromechanical switch (MEMS) devices, or other actuators 599. Any module described herein may (optionally) implement one or more such device(s) 520—as circuitry 417, 427, 447 of FIG. 4, for example, optionally comprising valves 551, 552 configured to control respective ones of dispensers 413, 423, 443, 444.

In some variants, for example, one or more instances of circuitry 417, 427 may implement device(s) 520 comprising one or more sensors 587 operable for accepting an indication of or otherwise responding to a departure of module 410 or some other artificial device from within a vicinity of a module in the digestive tract. Detecting such separations may reliably indicate an unsuccessful deployment, for example, causing circuitry 417 to close or not open one or more valves 551, 552. Circuitry 417 may include logic 573 for controlling a decision of whether to commence operation of one or more extended-release dispensers 413 configured for dispensing a statin or similar therapeutic agent, for example, in response to output from one or more such sensors 587.

Alternatively or additionally, one or more such modules 461, 463 may comprise one or more instances of antenna 562 (of circuitry 427) or some other element 426 operable for accepting an indication of or otherwise responding to a magnetic field from within a portion of the digestive tract. Element 426 may thus tend to align (or resist misalignment) with either of the other modules as shown, for example, if implemented as a permanent magnet or paramagnetic material. While in the digestive tract, moreover, such flux-guiding elements may be drawn to a tract wall by an external device such as a permanent magnet (on a belt, for example). Alternatively or additionally, antenna 562 may be used to receive signals in the form of such magnetic fields, to communicate sensor or other event data or to receive instructions as described herein.

In some variants, for example, any "first" or "second" module as described herein may implement device(s) 520 comprising one or more sensors 585 operable for accepting an indication of or otherwise responding to a temperature, pH, pressure, conductivity, or other environmental attribute indicating a particular portion of the digestive tract. Circuitry 427 may (optionally) include logic 572 for controlling a decision of whether to activate one or more extended-release dispensers 413 of an antibiotic or other therapeutic agent, for example, in response to output from one or more such sensors 585.

In some variants, for example, any "second" or "third" module as described herein may implement device(s) 520 comprising one or more sensors 582 operable for accepting an indication of or otherwise responding to a proximity to an artificial device from within a portion of the digestive tract. Any implementation of device(s) 520 as described herein may likewise comprise one or more instances of components 589 operable for accepting an indication of or otherwise responding to a concentration-indicative environmental attributes: sensors 584 for measuring or otherwise detecting a higher-than-nominal concentration of lipids, sensors 581 for measuring or otherwise detecting a higher-than-nominal concentration of alcohol or other controlled substances, sensors 586 for measuring or otherwise detecting a higher-than-nominal concentration of glucose or other carbohydrates, or sensors 583 for measuring or otherwise detecting a higher-than-nominal concentration of an artificial control marker. Such a control marker may include a specific ratio of two or more rare isotopes, for example, operative to trigger device(s) 520 to take some desired action and conveniently administrated (as a beverage, for example). Any "second" or "third" module as described herein may optionally include software, circuitry or other logic 571 for effectively controlling a decision of which controlled-release dispensers 413, 414 to activate, for example, in response to respective output from one or more such sensors 581-587 or other components 589. Alternatively or additionally, any "first" or "second" module as described herein may optionally include software, circuitry or other logic 571 for effectively controlling a decision of which controlled-release dispensers 443, 444 to activate, for example, in response to respective output from one or more such sensors 581-587 or other components 589. Any arithmetic, logical or other combination of such output may likewise be used for controlling any one such dispenser, and those skilled in the art will recognize many such suitable combinations in light of teachings herein. A "second" or "third" module 495 may contain any or all of sensors 581-587 or other device(s) 520, for example. Such other devices may, for example, include memory 530 configured for receiving measurement data 535 obtained thereby. Alternatively or additionally, memory 530 may include an instruction sequence or other code 532 configured for enabling processor 540 to decide whether to signal an apparent disintegration of the tethered group to which it belongs, for example, to user interface 510.

In light of teachings herein, numerous existing techniques may be applied for acquiring or using measurements or other detectable phenomena relating to a digestive tract for various functions as described herein without undue experimentation. See, e.g., U.S. Pat. No. 7,217,245 ("Noninvasive methods for detecting abnormalities in a subject such as disease or dysfunction"); U.S. Pat. No. 7,160,731 ("Examination method of buffer capacity of saliva and examination instrument of buffer capacity of saliva"); U.S. Pat. No. 7,155,269 ("Stress evaluation apparatus"); U.S. Pat. No. 7,062,306 ("Spectroscopy illuminator with improved delivery efficiency for high optical density and reduced thermal load"); U.S. Pat. No. 6,365,128 ("Monitoring gastrointestinal function to guide care of high risk patients"); U.S. Pat. No. 6,264,611 ("Monitor for interventional procedures"); U.S. Pat. No. 6,258,046 ("Method and device for assessing perfusion failure in a patient by measurement of blood flow"); U.S. Pat. No. 6,125,293 ("Method for determining the pH in the mucosa of the stomach or the gastrointestinal tract"); U.S. Pat. No. 5,833,625 ("Ambulatory reflux monitoring system"); U.S. Pat. No. 5,263,485 ("Combination esophageal catheter for the measurement of atrial pressure"). Those skilled in the art will also recognize how to apply numerous existing techniques for taking provisional, alternate, overlapping, or completion actions relating to such decisions as exemplified herein without undue experimentation, in light of these teachings. Such variations may be implemented in special purpose instructions or code 532 in memory 530 or other logic 570, for example, optionally implemented in special purpose circuitry comprising one or more sensors 581-587 or other components 589 configured for automatic decision making. Combinations of these may each be effectuated by comparative, arithmetic, conjunctive, or other operators relating each pairing of input 518 or other detectable determinants described with reference to FIG. 5, for example.

Figure 6:
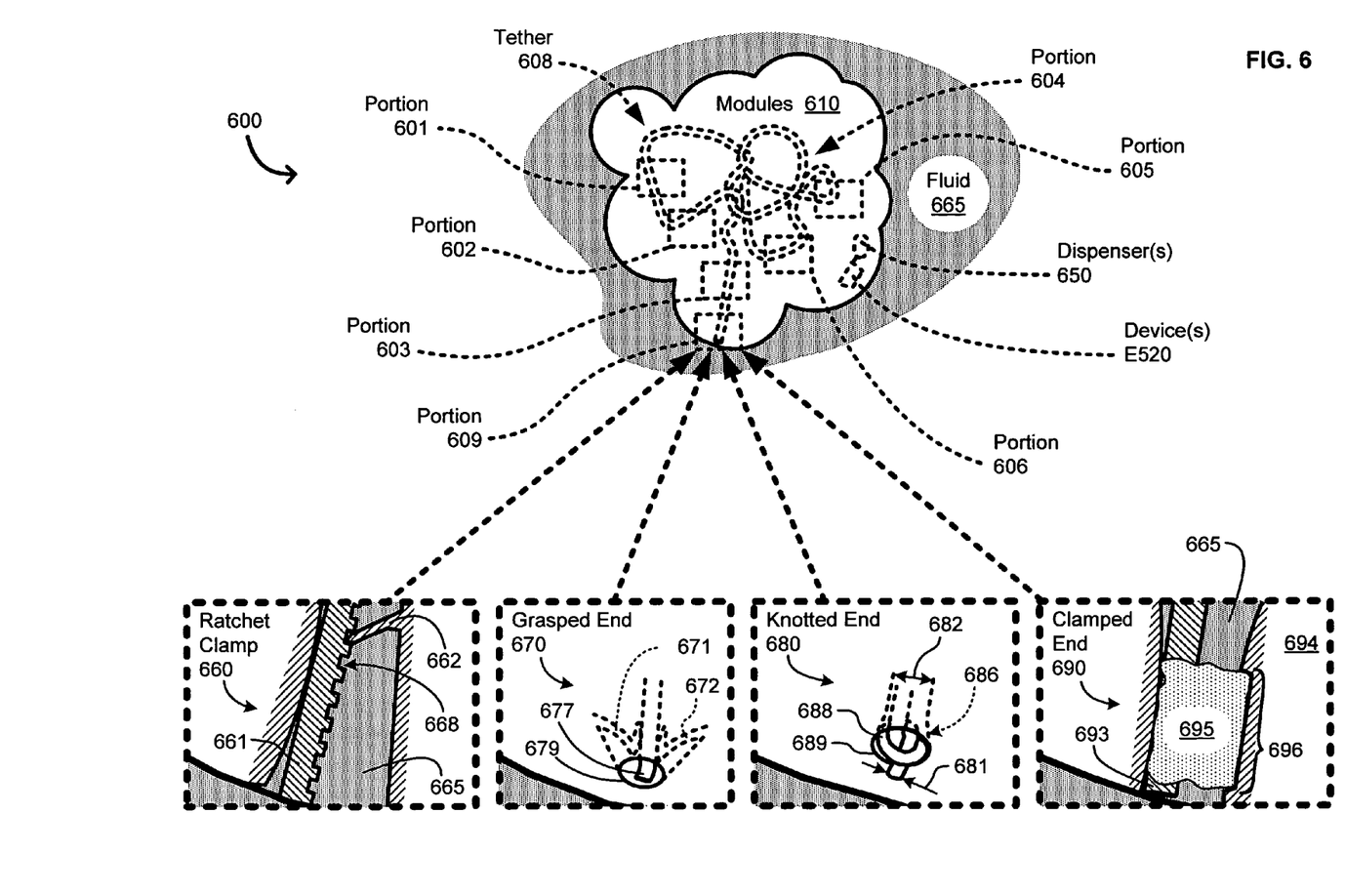
FIG. 6 shows a digestive tract interaction system having at least one tether binding several non-aligned modules.

With reference now to FIG. 6, shown is an example of a system that may serve as a context for introducing one or more processes and/or devices described herein. As shown system 600 may include at least one tether 608 binding several non-aligned modules 610 within fluid 665. Tether 608 may comprise first and second distal portions 609 bounding a "middle" portion 604 containing or otherwise overlapping one or more other portions 601, 602, 603, 605, 606. Each of modules 610 is roughly of similar size and small enough to pass through an entire digestive tract containing fluid 665 (at least after an appropriate deflation). Tether 608 effectively couples a "first" and "second" ones of modules 610 via a gap in (at least) a "third" module, tether 608 having at least a middle portion 604 configured to slip free from the "third" module responsive to the tether breaking or being released.

In some embodiments, any "first" or "second" module as described herein may comprise a ratchet clamp 660 comprising one or more flexible members 662 extending into one or more corresponding recesses 668 of tether 661 so that tether 661 can be pulled outward (downward as shown) from the module but resists retraction. In some variants of system 200 (of FIG. 2), for example, such a mechanism can be used by inner sleeve 215 to remove slack from (and optionally place static tension into) at least a middle portion of tether 233. Excess length of tether 233 can then be pulled free (if notched or perforated, for example) or cut off (with a cutting device of inner sleeve 215, for example, not shown).

Alternatively or additionally, any "first" or "second" module as described herein may comprise a grasped (tether) end 670 comprising one or more flexible members 671, 672 gripping a rotationally symmetric portion of an end of tether 677 at an orifice 679 (such as may implement distal portion 609 of tether 608). In some variants, such flexible members 671 may be calibrated so that they will release tether 679 in response to a predetermined tensile force (upward as shown) urging tether 679 to be released by the module. In some variants, a tether 679 includes a smooth distal portion 609, facilitating the release of such modules from the "second" module, for example.

Alternatively or additionally, any "second" or "third" module as described herein may comprise a knotted (tether) end 680 in which a stopper or other suitable knot 688 is used in conjunction with a bore 689 having a cross-sectional diameter 682 larger than a cross-sectional diameter 681 of the tether but smaller than that of the knot 688. The bore may (optionally) have a tapered portion 686 so that part of the bore is large enough to accommodate a portion of the knot.

Alternatively or additionally, any module as described herein may comprise a clamped end 690 in which an adhesive and/or expansive element 695 expands or otherwise emerges when exposed to fluid 665 (from one or more recessed portions 696 of module 694, for example) to secure a distal portion of a tether 693. Such clamping may result from adhesive activation and/or from a compression fit, for example, resulting from element 695 reacting to water in fluid 665.

In some embodiments, system 600 comprises several ("first," "second," and "other") modules 610 bound by tether 608, optionally for deployment via a flexible catheter or soft gelatin capsule into an animal needing treatments over an extended period (of several days or months, for example). Any or all such modules 610 may each comprise one or more instances of device(s) 520 (of FIG. 5) controlling one or more dispensers 650 and/or a unitary body having an overall average density smaller than 0.9 grams per milliliter. In some embodiments, for example, enough buoyant modules may be included so that the overall average density of system 600 is smaller than that of fluid 665.

In some embodiments, a therapeutic agent may be placed into one or more dispensers 650 described herein, optionally packaged with one or more solid or gel phase carriers or excipients. Examples of such carriers or excipients include, but are not limited to, croscarmellose sodium, povidone, microcrystalline cellulose, calcium carbonate, calcium phosphate, various sugars, starches, cellulose derivatives, gelatin, pregelatinized starch, polymers such as polyethylene glycols, lactose, lactose monohydrate, sucrose, talc, gelatin, agar, pectin, acacia, magnesium stearate, stearic acid and substantially any combination thereof.

In some embodiments, therapeutic agents that are hydrophobic may be packaged through use of a cosolvent system comprising benzyl alcohol, a nonpolar surfactant, a water-miscible organic polymer, and an aqueous phase. The cosolvent system may be the VPD co-solvent system. VPD is a solution of 3 percent weight/volume benzyl alcohol, 8 percent weight/volume of the nonpolar surfactant polysorbate 80, and 65 percent weight/volumen polyethylene glycol 300, made up to volume in absolute ethanol. The VPD co-solvent system (VPD:5W) consists of VPD diluted 1:1 with a 5 percent dextrose in water solution. This co-solvent system dissolves hydrophobic therapeutic agents well, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol (i.e., polyvinyl pyrrolidone; and other sugars or polysaccharides may substitute for dextrose). Many other delivery systems may be used to administer hydrophobic therapeutic agents as well. For example, liposomes and emulsions are well known examples of delivery vehicles or carriers for hydrophobic drugs. Certain organic solvents such as dimethysulfoxide also may be employed, although usually at the cost of greater toxicity.

Some therapeutic agents may be packaged as salts with pharmaceutically compatible counter ions. Pharmaceutically compatible salts may be formed with many acids, including hydrochloric, sulfuric, acetic, lactic, tartaric, malic, succinic, etc. Salts of therapeutic agents tend to be more soluble in aqueous or other protonic solvents than are the corresponding free-base forms.

Numerous carriers and excipients are known and are commercially available (i.e., The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, 58th Edition, Thompson, P D R, Montvale, N.J. 2004; U.S. Pat. Nos. 6,773,721; 7,053,107; 7,049,312 and Published U.S. Patent Application No. 20040224916; herein incorporated by reference to the extent not inconsistent herewith). In some embodiments, such methods may be used with regard to one or more dietary or other regimen compliance objectives and/or combinations of one or more pharmaceutical or nutraceutical agents with one or more aspects of diet, or other subject attributes.

One or more instances of tethers 608 among modules 610 may (optionally) include one or more elastic (length) portions 601 each operable for a nominally elastic deformation of at least 10%. (Middle portion 604 contains or otherwise at least overlaps elastic portion 601.) In some variants system 600 is configured with one or more such elastic portions 601 totaling at least half of (an entire length of) tether 608. Alternatively or additionally, tethers described herein may comprise one or more inelastic portions 602 (of middle portion 604) optionally including a notch or other configured breakage mechanism. In some contexts, nominally "inelastic" length portions normally deform permanently or break if stretched by 10% or more.

In some variants, tethers described herein may likewise comprise one or more instances of soluble portions 603 accessible by fluid 665 only when exposed by an activation of one or more piezoelectric transducers 592, shape-memory element 593, springs, or other actuators 599. One or more such actuators 599 may open or otherwise control one or more valves 551, 552 selectively in response to logic 570 as described herein, for example. Alternatively or additionally, one or more instances of tethers 608 may comprise middle portion 604 at least some of which is semi-soluble or substantially insoluble in one or more digestive fluids 665 in a typical stomach or other intended environments.

In some embodiments, a "semi-soluble" element is one that is configured to break down in more than an hour but less than a week, and a "substantially insoluble" element is less soluble than this. Numerous water insoluble polymers may be used to reduce a compound's solubility, for example, such as cellulose derivatives (i.e., ethylcellulose), polyvinyl acetate, neutral copolymers based on ethyl acrylate and methylmethacrylate, copolymers of acrylic and methacrylic acid esters with quaternary ammonium groups, or the like. In some embodiments, polymers used in forming such less-soluble elements may be plasticized. Examples of plasticizers that may be used for this purpose include, but are not limited to, triacetin, tributyl citrate, triethyl citrate, acetyl tri-n-butyl citrate diethyl phthalate, castor oil, dibutyl sebacate, acetylated monoglycerides, or the like and/or substantially any combination thereof. In some embodiments, one or more such plasticizers may be present at about 3 to 30 weight percent and more typically about 10 to 25 weight percent based on the polymer to which the plasticizer is added. The type of plasticizer and its content depends on the polymer or polymers and/or the nature of the coating system.

In some embodiments, water-soluble nonionic polysaccharide derivatives may be used to wrap one or more therapeutic agents for rapid release. For example, hydroxypropylmethylcellulose, hydroxypropylcellulose, and/or sodium carboxymethylcellulose may be used. Such polymers form coatings that quickly dissolve in digestive fluids or water and have a high permeability. Accordingly, in some embodiments, such polymers may be used for rapid release of one or more therapeutic agents that are wrapped in such a wrapper following administration to an individual.

In some embodiments, one or more therapeutic agents may be wrapped in a wrapper that provides for sustained release of the one or more therapeutic agents. For example, one or more therapeutic agents may be released continuously over twelve hours through use of wrappers constructed from ethyl cellulose and an ethyl acrylate-methyl methacrylate-ethyl trimethylammoniumchloride methacrylate copolymer as the release controlling wrapper. Existing methods and materials that may be used to prepare such wrappers are known by those skilled in the art and are commercially available (i.e., Rohm Pharma, Piscataway, N.J.; U.S. Pat. Nos. 6,656,507; 7,048,945; 7,056,951; hereby incorporated by reference to the extent not inconsistent herewith).

In some embodiments, tethers described herein may be made integrally with one or more modules and/or include one or more strands of surgical thread, polymer, or other materials of suitable elasticity and strand structure. In many contexts, tether 608 may be implemented to include one or more other instances of soluble portions 605, dispensers 650 (optionally controlled by device(s) 520), or inelastic portions 606 (of middle portion 604). In some variants, for example, inelastic portion 606 may be configured to separate when loaded with more than a calibrated tension T, where T is at least 1-10 pounds and/or at most 10-100 pounds. Tether 608 may, for example, be configured as a compound structure that includes one or more modules joining two or more tether segments end-to-end. Tether 468 may likewise be formed as a loop, for example, by module 461 grasping both ends of a simple tether passing through other modules 462, 463.

In an embodiment in which system 600 comprises more than three modules 610 each small enough to pass through a specific digestive tract, a "fourth" one of modules 610 may (optionally) engage at least one end (e.g. distal portion 609) of tether 608. Alternatively or additionally, in many applications, modules 610 may be few enough, inert enough, or otherwise implemented on a small enough scale so that their one or more dispensers 650 may be operable for dispensing a total of at most 15 grams of medicinal material. A fraction of modules 610 may lack dispensers, for example, especially if configured for one or more other specialty functions. System 600 may implement a version of tethered group 490 as described herein, for example, in which module 492 is inflatable, in which module 493 comprises one or more implementations of device(s) 520 operable for external communication, in which module 494 includes one or more actuators 599 operable for severing or otherwise manipulating tether 498, in which module 495 comprises one or more cameras or other components 589 operable for data capture, and/or in which module 496 performs one or more other resource-intensive specialty functions. Such systems 600 may be assembled from inventories of diverse-looking modules 410, 420, 430, 440 within a local care facility, for example, based upon information available just before deployment into a digestive tract.

Figure 7:
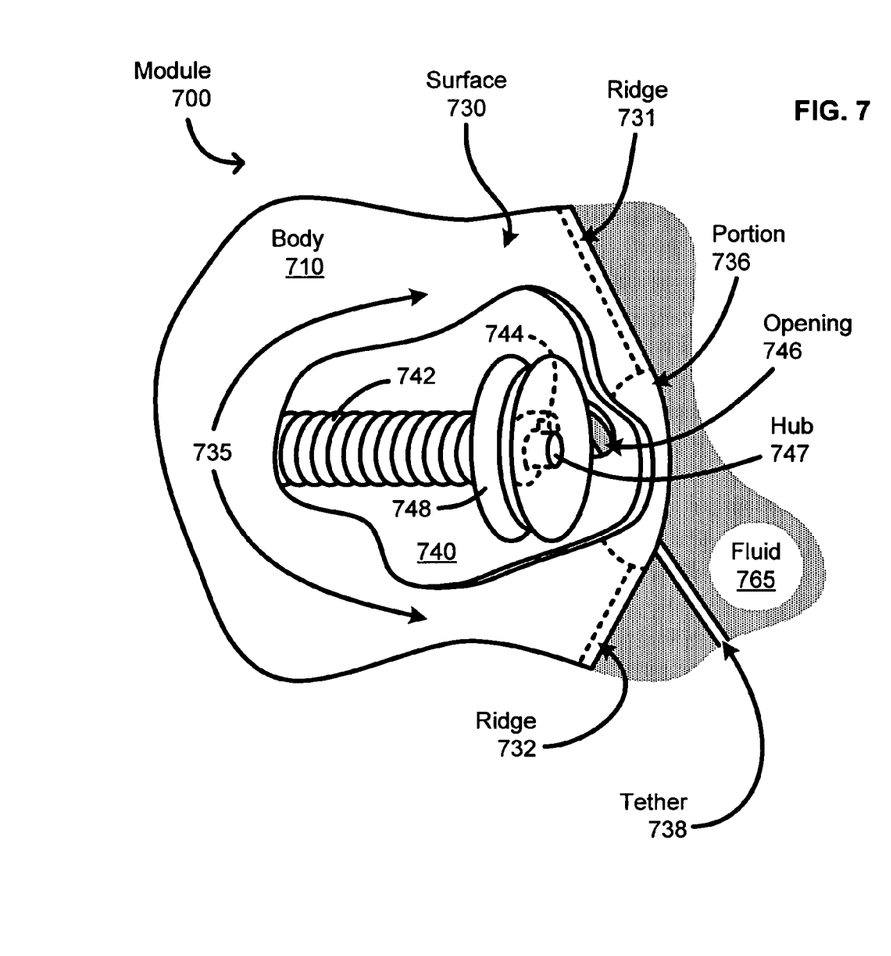
FIG. 7 shows a system module containing at least one spool operable to retract a portion of a tether by rotating about a hub.

With reference now to FIG. 7, shown is an example of a system that may serve as a context for introducing one or more processes and/or devices described herein. As shown system module 700 may include at least one unitary body 710 having an external surface 730 comprising at least one convex portion 736, at least one saddle region 735, at least two (at least partly convex) ridge regions 731, 732, and at least one opening 746. A cutaway reveals chamber 740 within module 700 containing at least one spool 748 operable to retract a (rotationally symmetric or asymmetric) portion of tether 738 by rotating about hub 747. Metallic or other deformable windings 742 are pre-loaded (under tension, e.g.) so that spool 748 is urged counter-clockwise (as shown), which torque is initially resisted by one or more soluble or semi-soluble latches 744. When body 710 is immersed enough so that suitable digestive or other fluid 765 enters chamber 740, however, fluid 765 dissolves the latch(es) 744, freeing spool 748 to draw in 1% or more of (the length of) tether 738.

Figure 8:
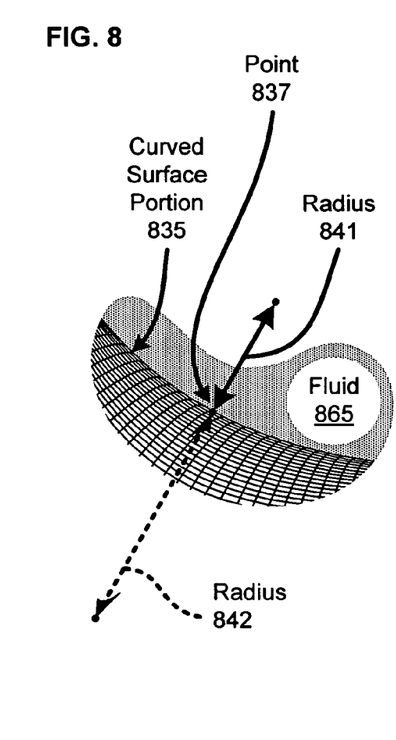
FIG. 8 shows a curved surface portion (saddle region) of a module a digestive tract interaction system.

With reference now to FIG. 8, shown is an example of a curved surface portion 835 that may serve as a context for introducing one or more processes and/or devices described herein. Curved surface portion 835 defines a saddle region, one in which each point 837 has an outer (e.g. upper side, facing fluid 865) radius 841 of curvature in one plane and an inner (e.g. lower side) radius 842 of curvature in an orthogonal plane.

Referring again to FIG. 7, unitary body 710 may optionally have a total external surface 730 of which at least 1% comprises one or more saddle regions 735. Several other modules 420, 430, 494, 497 are likewise described herein that may optionally have such widely grooved surfaces to facilitate a safe retention of such modules within a corresponding gastric compartment. One or more modules 494, 496 protruding from tethered group 490 may (optionally) be configured each as a unitary body having an external surface area of which at least 5% comprises a saddle region.

Figure 9:
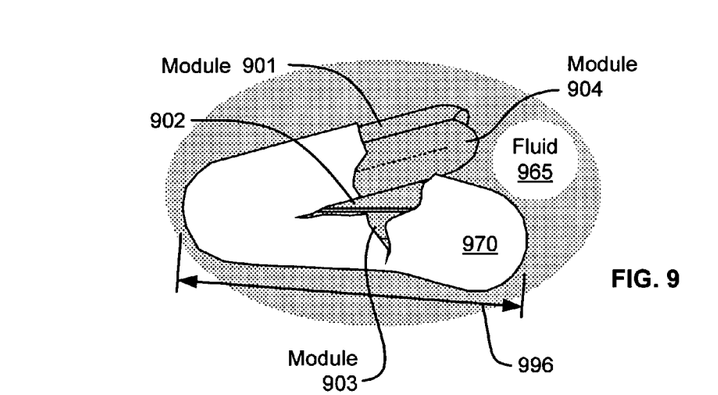
FIG. 9 shows a capsule immersed in digestive fluid that has dissolved enough so that a structure of several elongate modules therein has begun to unfold.

With reference now to FIG. 9, shown is an example of a capsule 970 immersed in digestive fluid 965. As shown, capsule 970 has dissolved enough so that several modules 901, 902, 903, 904 have begun to unfold. Capsule 970 may optionally be more than twice as long as its width (as shown) and/or be small enough to be swallowed comfortably by a subject (e.g. by having a length 996 about 1-2 times that of an eyeball of the subject). For a typical human adult, for example, length 996 may be longer than 2 centimeters and/or less than 5 centimeters.

Figure 10:
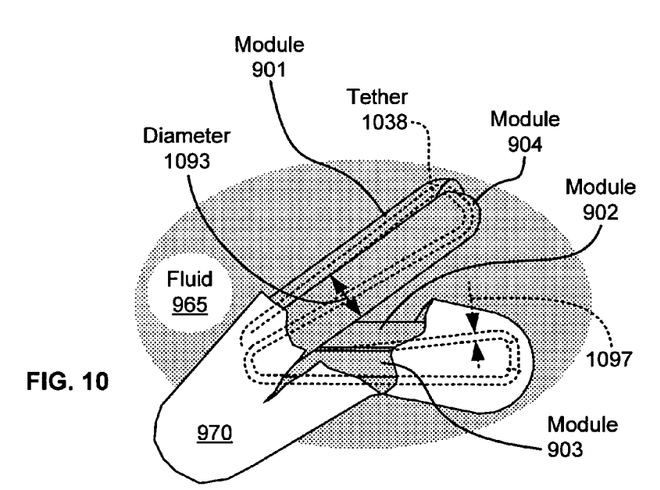
FIG. 10 shows the capsule of FIG. 9, further dissolved so that the elongate modules have almost emerged.

With reference now to FIG. 10, shown is an example of the capsule 970 of FIG. 9, further dissolved in digestive fluid 965 so that modules 901-904 have almost emerged in response to tension in tether 1038. Each of modules 901-904 may have a unitary body with an average cross-sectional diameter 1093. Tether 1038 may have an average cross-sectional diameter 1097 less than ⅓ of the average cross-sectional diameter 1093 of modules 901-904. In some variants, tether 1038 may be configured to retract lengthwise or otherwise become taut in response to immersion in digestive fluid 965.

Figure 11:
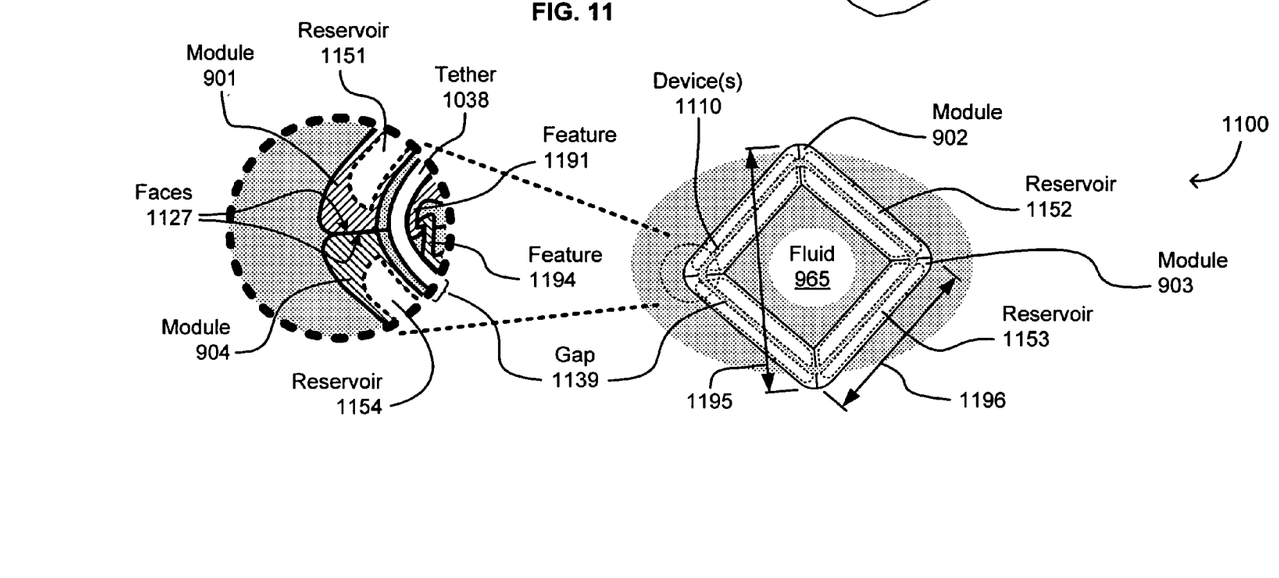
FIG. 11 shows the elongate modules of FIG. 9 in a fully expanded configuration.

With reference now to FIG. 11, shown is an example of the modules 901-904 of FIGS. 10-11 in a fully expanded configuration. For a typical human adult, for example, length 1195 may be longer than 3 centimeters and/or less than 7 centimeters. As shown, modules 901-904 each has a nominal module length 1196 more than twice as long as its (respective) average cross-sectional diameter 1093. At least two of the modules 902, 903 each have one or more respective reservoirs 1152, 1153. In some variants, each such reservoir 1152, 1153 may contain a respective therapeutic agent or a partial dosage of a common therapeutic agent. Alternatively or additionally, each such reservoir 1152, 1153 may be configured for dispensation under respectively different conditions.

To maintain this expanded configuration, in some variants, each adjacent pair of modules may advantageously include a magnetic, adhesive, mechanical, or other latching feature. Module 901 may optionally be configured with one or more protruding features 1191 able to extend into module 904, for example. Alternatively or additionally, module 904 may likewise include one or more protruding features 1194 able to extend into module 901. Such features 1191, 1194 may latch together as shown or otherwise engage as respective beveled faces 1127 thereof come into contact. Tether 1038 may (optionally) be configured to support such contact, such as by pressing feature 1191 into latching engagement with feature 1194.

System 1100 exemplifies a digestive tract interaction system comprising several modules 901-904 of similar size and each small enough to pass through a digestive tract of a suitable subject. Tether 1038 may be configured as a taut loop effectively coupling each pair of these modules 901-904 via a gap 1139 in each of the modules. In a variant in which one or more device(s) 1110 is configured to sever or otherwise release respective ends of tether 1038 within gap 1139 of module 901, for example, the gaps 1139 of one or more other modules 902-904 are large enough to permit tether 1038 to slip free so that all of the modules 901-904 can pass separately and safely per vias naturales. Such device(s) 1110 may (optionally) be configured to effect such a release in response to a pH, a sensed position, a temperature, a remote control signal, an excessive force, or some other indication that system 1100 should not be fully expanded. Device(s) 1110 may instantiate one or more device(s) 520 of FIG. 5, for example, permitting a care provider to abort a deployment of system 1100 in the event that system 1100 has apparently deployed in an esophagus or small intestine, for example. In some variants, for example, one or more other reservoirs 1151, 1154 may comprise a dispenser containing one or more of an antiviral or other antimicrobial agent, or some other therapeutic material.

In light of teachings herein, numerous existing techniques may be applied for forming or assembling components of modules suitable for use in various portions of a digestive tract for various functions as described herein without undue experimentation. See, e.g., U.S. Pat. No. 7,182,957 ("Polymer blends that swell in an acidic environment and deswell in a basic environment"); U.S. Pat. No. 7,097,851 ("Oral formulation for gastrointestinal drug delivery"); U.S. Pat. No. 7,041,083 ("Medical catheter assembly including a removable inner sleeve and method of using the same"); U.S. Pat. No. 6,797,283 ("Gastric retention dosage form having multiple layers"); U.S. Pat. No. 6,120,803 ("Prolonged release active agent dosage form adapted for gastric retention"); U.S. Pat. No. 5,198,229 ("Self-retaining gastrointestinal delivery device"); U.S. Pat. No. 4,522,625 ("Drug dispenser comprising wall formed of semipermeable member and enteric member"); U.S. Pat. Pub. No. 2007/0178160 ("Gastro-intestinal device and method for treating addiction"); U.S. Pat. Pub. No. 2007/0106213 ("Gastrointestinal applicator and method of using same"); U.S. Pat. Pub. No. 2006/0068003 ("System for increasing compliance with medication regime"); U.S. Pat. Pub. No. 2005/0249799 ("Polymeric drug delivery system for hydrophobic drugs"); U.S. Pat. Pub. No. 2005/0201974 ("Bioadhesive polymers with catechol functionality"); U.S. Pat. Pub. No. 2005/0058701 ("Active drug delivery in the gastrointestinal tract"); U.S. Pat. Pub. No. 2004/0224019 ("Oral controlled release system for targeted drug delivery into the cell and its nucleus for gene therapy, DNA vaccination, and administration of gene based drugs"); U.S. Pat. Pub. No. 2004/0109894 ("pH triggered targeted controlled release systems for the delivery of pharmaceutical active ingredients"); U.S. Pat. Pub. No. 2003/0232078 ("Formulation & dosage form for the controlled delivery of therapeutic agents"); U.S. Pat. Pub. No. 2003/0113371 ("Composition and method for maintaining blood glucose level by employing the hydrophilic matrix based oral controlled release antidiabetic composition"). Those skilled in the art will also recognize how to apply numerous existing techniques for taking provisional, alternate, overlapping, or completion actions relating to such decisions as exemplified herein without undue experimentation, in light of these teachings. Such variations may be implemented in special purpose instructions or code 532 in memory 530 or other logic 570, for example, optionally implemented in special purpose circuitry comprising one or more sensors 581-587 or other components 589 configured for automatic decision making. Combinations of these may each be effectuated by comparative, arithmetic, conjunctive, or other operators relating each pairing of determinants described herein, for example.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f)

a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A digestive tract interaction system comprising:
a first module small enough to pass through a digestive tract;
a second module small enough to pass through the digestive tract and at least 10% as large as the first module, the second module including a unitary body at least half as long as the first module, a dispenser containing medicinal material, and one or more sensors configured to detect a concentration of at least one of a lipid, a carbohydrate, or an artificial control marker;

a third module small enough to pass through the digestive tract and at least 10% as large as the second module; and a tether effectively coupling the first module with the second module via at least a gap in the third module, the tether having at least a middle portion configured to slip free from the third module responsive to the first module decoupling from the second module.

2. The digestive tract interaction system of claim 1 in which the second module comprises:
one or more valves each configured to control a material dispensation.

3. The digestive tract interaction system of claim 1 in which the third module is at least 10% as voluminous as the second module.

4. The digestive tract interaction system of claim 1 in which the third module comprises:
at least a bore forming the gap.

5. The digestive tract interaction system of claim 1 in which the tether comprises:
at least an elastic portion of the middle portion.

6. The digestive tract interaction system of claim 1 further comprising:
a fourth module supported by the tether and comprising one or more actuators.

7. The digestive tract interaction system of claim 1 in which the second module comprises:
one or more sensors responsive to a departure of an artificial device from within a portion of the digestive tract.

8. The digestive tract interaction system of claim 1 in which the second module comprises:
one or more sensors responsive to an environmental attribute indicating a portion of the digestive tract.

9. The digestive tract interaction system of claim 1 in which the one or more sensors comprise:
one or more sensors configured to detect a concentration of at least one of a lipid or an artificial control marker.

10. The digestive tract interaction system of claim 1 in which the one or more sensors comprise:
one or more sensors configured to detect a concentration of at least one of a lipid or a carbohydrate.

11. The digestive tract interaction system of claim 1 in which the one or more sensors comprise:
one or more sensors configured to detect a concentration of at least one of a carbohydrate or an artificial control marker.

12. The digestive tract interaction system of claim 1 in which the tether comprises:
the tether having one or more elastic portions totaling at least half of an entire length of the tether.

13. A digestive tract interaction system comprising:
a first module small enough to pass through a digestive tract;
a second module small enough to pass through the digestive tract and at least 10% as large as the first module;
a third module small enough to pass through the digestive tract and at least 10% as large as the second module, the third module including a unitary body at least half as long as the first module, a dispenser containing medicinal material, and one or more sensors configured to detect a concentration of at least one of a lipid, a carbohydrate, or an artificial control marker; and
a tether effectively coupling the first module with the second module via at least a gap in the third module, the tether having at least a middle portion configured to slip free from the third module responsive to the first module decoupling from the second module.

14. The digestive tract interaction system of claim 13 in which the third module comprises:
one or more valves each configured to control a material dispensation.

15. The digestive tract interaction system of claim 13 in which the third module is at least 10% as voluminous as the second module.

16. The digestive tract interaction system of claim 13 in which the third module comprises:
at least a bore forming the gap.

17. The digestive tract interaction system of claim 13 further comprising:
a fourth module supported by the tether and comprising one or more actuators.

18. The digestive tract interaction system of claim 13 in which the third module comprises:
one or more sensors responsive to a departure of an artificial device from within a portion of the digestive tract.

19. The digestive tract interaction system of claim 13 in which the third module comprises:
one or more sensors responsive to an environmental attribute indicating a portion of the digestive tract.

20. The digestive tract interaction system of claim 13, further comprising:
a capsule containing at least the first, second, and third module.

21. The digestive tract interaction system of claim 13 in which the one or more sensors comprise:
one or more sensors configured to detect a concentration of at least one of a lipid or an artificial control marker.

22. The digestive tract interaction system of claim 13 in which the one or more sensors comprise:
one or more sensors configured to detect a concentration of at least one of a lipid or a carbohydrate.

23. The digestive tract interaction system of claim 13 in which the one or more sensors comprise:
one or more sensors configured to detect a concentration of at least one of a carbohydrate or an artificial control marker.

24. The digestive tract interaction system of claim 13 in which the tether comprises:
the tether having one or more elastic portions totaling at least half of an entire length of the tether.

* * * * *